United States Patent [19]

Corn, Jr.

[11] 4,024,194

[45] May 17, 1977

[54] PROCESS FOR THE PURIFICATION OF 9,9-BIS(4-HYDROXYPHENYL)-FLUORENE

[75] Inventor: John E. Corn, Jr., Schenectady, N.Y.

[73] Assignee: General Electric Company, Schenectady, N.Y.

[22] Filed: Mar. 16, 1976

[21] Appl. No.: 667,461

[52] U.S. Cl. .................. 260/619 A; 260/619 R; 260/619 D; 260/619 F

[51] Int. Cl.$^2$ .................................. C07C 37/24

[58] Field of Search ....... 260/619 A, 619 D, 619 F, 260/619 R

[56] References Cited

OTHER PUBLICATIONS

Morgan, "Macromolecules" vol. 3, p. 536 (1970).

Primary Examiner—Norman Morgenstern
Attorney, Agent, or Firm—Joseph T. Cohen; Jerome C. Squillaro

[57] ABSTRACT

Certain impurities found in 9,9-bis(4-hydroxyphenyl)-fluorene are removed by treatment of the latter with nitromethane in which the impurity is soluble, and thereafter isolating the purified fluorene.

2 Claims, No Drawings

PROCESS FOR THE PURIFICATION OF 9,9-BIS(4-HYDROXYPHENYL)-FLUORENE

The Government has rights in this invention pursuant to Contract No. N00019-74-C-0174 awarded by the Department of the Navy.

PURIFICATION OF FLUORENES

This invention is concerned with a process for purifying a bisphenol fluorene. More particularly, the invention is concerned with removing from 9,9-bis(4-hydroxyphenyl)-fluorene (hereinafter called BPF) having the formula

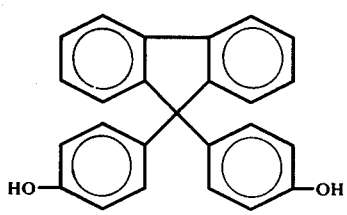

the impurity 9-(4-hydroxyphenyl)-9(2-hydroxyphenyl)-fluorene having the formula

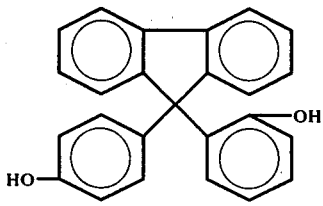

by treatment of the mixture of the two fluorenes with nitromethane in which the impurity is soluble, and thereafter isolating the desired BPF.

The above-identified BPF of formula I can be prepared in the manner disclosed by P. W. Morgan in *Macromolecules*, Volume 3, page 536 (1970), whereby fluorenone is reacted with phenol in the presence of β-mercapto propionic acid and anhydrous HCl. When this reaction is carried out, it is found that a good yield of desired BPF is obtained, but it is contaminated by the isomer identified by formula II.

BPF can be used to make various polymer compositions. For instance, the BPF can be reacted with phosgene to make polycarbonate resins, or else it can be reacted with organic acyl dihalides such as terephthaloyl chloride, isophthaloyl chloride, etc., to make polyester resins. Alternatively, the BPF can be reacted with nitro-N-methylphthalimides in the manner described in the copending application of Clayton B. Quinn, Ser. No. 553,658 filed Feb. 27, 1975, now U.S. Pat. No. 3,944,583 issued Mar. 16, 1976, to form intermediate precursors which upon further processing can yield novel dianhydrides. The latter can in turn be reacted with organic diamines to make polyimide resins of the type more particularly disclosed and claimed in the copending application of the aforesaid Clayton B. Quinn Ser. No. 553,659, also filed Feb. 27, 1975, now U.S. Pat. No. 3,968,083 issued July 6, 1976. By reference these two patent applications, both of which are assigned to the same assignee as the present invention, are made part of the disclosures and teachings of the instant application. Resinous compositions obtained from the BPF have been found to have good flammability resistance and oxygen indices, which make them useful in applications where resistance to elevated temperatures is desirable, for instance, as insulation for electrical conductors, as motor slot liners, as films, and as high temperature coatings.

When using the BPF, it is important that the impurity of formula II be significantly reduced and preferably removed from the BPF since the presence of the impurity results in low molecular weight products when the BPF is used for polymer formation. This interferes with obtaining compositions of the desired properties required for molding, extruding, or other applications.

I have now discovered that I am able to remove the impurity of formula II from the BPF by employing nitromethane as a means for extracting the impurity in a simple step to leave behind the desired BPF of the requisite purity. In accordance with my invention, the BPF containing the impurity of formula II, is mixed with nitromethane, preferably in an amount sufficient to solubilize all of the impurity therein. This mixture is then heated to an elevated temperature to insure solubilization of all ingredients in the nitromethane, removing any solid material while the solution is still hot, and then cooling the mixture to below 30° C., at which point the BPF will settle out as a crystalline material and the impurity will remain dissolved in the nitromethane. Removal of the solid material and washing of the latter with additional nitromethane, and advantageously with toluene, for instance, to remove anything else which may be desired, will give essentially pure BPF free of the impurity of formula II. The purified BPF will be found to have physical characteristics, such as melting point, almost identical with a pure sample. The amount of nitromethane generally used should advantageously, by weight, be within the range of from 1–20 parts of the nitromethane per part of the mixture of the BPF and the impurity. Generally the impurity of formula II will constitute about 5% of the total weight of the BPF.

In order that those skilled in the art may better understand how the present invention may be practiced, the following example is given by way of illustration and not by way of limitation.

EXAMPLE 1

297 grams of BPF containing about 5% by weight of the impurity of formula II, was charged to a 4-liter flask together with 1800 ml nitromethane. The mixture was slowly heated while stirring to 80° C. The light yellow solution which was obtained was filtered while hot and then allowed to cool slowly with stirring to 20° C. The solid which separated was collected, washed once with cold nitromethane (about 500 ml), once with 1 liter of toluene, and dried to yield 253 grams (85.2% yield) of BPF having a melting point range of 224.8°–225.4° C. This BPF was found to contain less than 0.5%, by weight, of the aforesaid impurity.

I claim:
1. The process for purifying 9,9-bis(4-hydroxyphenyl)-fluorene containing as an impurity therein 9-(4-hydroxyphenyl)-9(2-hydroxyphenyl)-fluorene which comprises (1) forming a solution of the aforesaid two fluorenes in an amount of nitromethane which at elevated temperatures is sufficient to form a homogeneous solution, (2) cooling the solution to precipitate the 9,9-bis(4-hydroxyphenyl)-fluorene, and (3) removing the nitromethane solution containing the impurity and leaving behind the essentially pure 9,9-bis(4-hydroxyphenyl)-fluorene.

2. The process as in claim 1 wherein the nitromethane solution is cooled to a temperature below 30° C in order to permit the 9,9-bis(4-hydroxyphenyl)-fluorene to settle out as a crystalline material.

* * * * *